(12) United States Patent
Burres

(10) Patent No.: US 9,918,878 B2
(45) Date of Patent: Mar. 20, 2018

(54) DEVICE AND METHOD FOR REMOVING EARWAX

(71) Applicant: Steven Burres, Beverly Hills, CA (US)

(72) Inventor: Steven Burres, Beverly Hills, CA (US)

( * ) Notice: Subject to any disclaimer, the term of this patent is extended or adjusted under 35 U.S.C. 154(b) by 0 days.

(21) Appl. No.: 15/007,808

(22) Filed: Jan. 27, 2016

(65) Prior Publication Data

US 2016/0135995 A1    May 19, 2016

Related U.S. Application Data

(60) Continuation of application No. 14/329,700, filed on Jul. 11, 2014, now abandoned, which is a continuation of application No. 13/926,381, filed on Jun. 25, 2013, now Pat. No. 8,777,972, which is a division of application No. 13/111,240, filed on May 19, 2011, now abandoned.

(51) Int. Cl.
*A61F 11/00* (2006.01)

(52) U.S. Cl.
CPC ................. *A61F 11/006* (2013.01)

(58) Field of Classification Search
CPC ...... A61F 11/006; A61F 13/38; A61M 35/006
See application file for complete search history.

(56) References Cited

U.S. PATENT DOCUMENTS

| | | |
|---|---|---|
| 1,450,612 A | 4/1923 | Schultz |
| 2,490,168 A | 12/1949 | Strauss |
| 3,923,061 A | 12/1975 | Rossignol |
| 4,820,259 A | 4/1989 | Stevens |
| 4,935,001 A | 6/1990 | George |
| 5,107,861 A * | 4/1992 | Narboni ................. A61F 13/38 128/846 |
| 5,509,921 A | 4/1996 | Karell |
| 5,632,756 A | 5/1997 | Kruglick |
| 5,715,559 A | 2/1998 | Mitri |
| 6,033,417 A | 3/2000 | Tseng |
| 6,155,987 A | 12/2000 | Scherl |
| 7,074,230 B2 | 7/2006 | Olson |
| 2003/0236540 A1 | 12/2003 | Mendez |
| 2006/0190020 A1 | 8/2006 | Eicoff |
| 2008/0300527 A1 | 12/2008 | Bivins |
| 2011/0066172 A1 | 3/2011 | Silverstein |

* cited by examiner

*Primary Examiner* — Anh Dang
(74) *Attorney, Agent, or Firm* — Trojan Law Offices

(57) ABSTRACT

The present invention describes an earwax removal device having varying structures to provide different earwax removal capabilities. In all designs, the overall contour of the earwax-extracting member resembles the dimensions of the external auditory canal and is flexible enough to conform to it during insertion. Each engages and collects wax using the pressure of insertion and rotation effects. Embodiments include a club-like member having multiple protrusions and extractions to collect wax along its sides, and an opening in the tip that leads to a channel to collect wax; a flexible spiral member to compress when the device is inserted in an ear and thereby extract wax as it expands when the device is removed; a screw-like structure to laterally move wax and grind as it rotates; a multi-channel structure to cut and collect wax simultaneously; and a shovel-like structure to effectively shear and scrape wax from an ear canal.

12 Claims, 12 Drawing Sheets

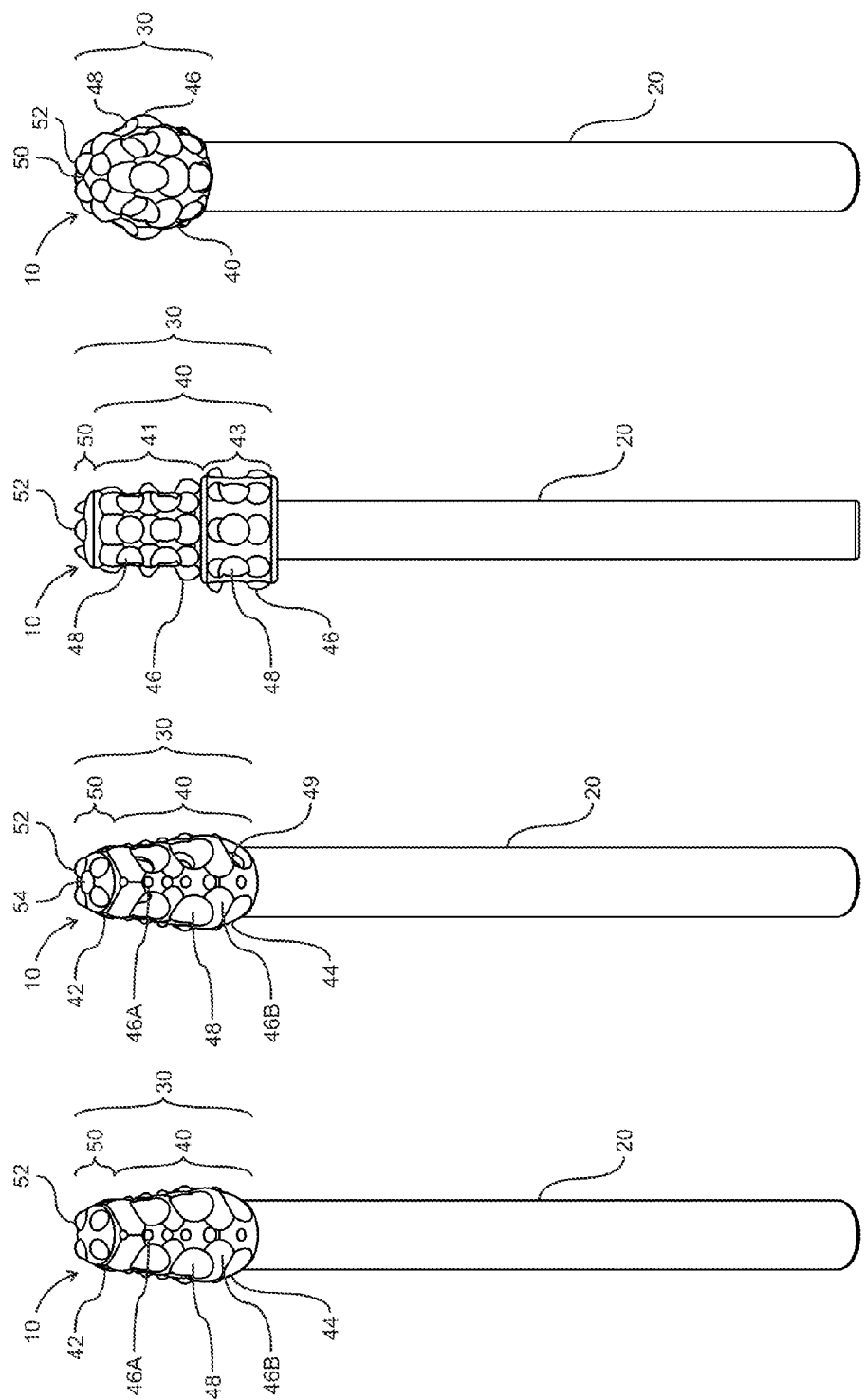

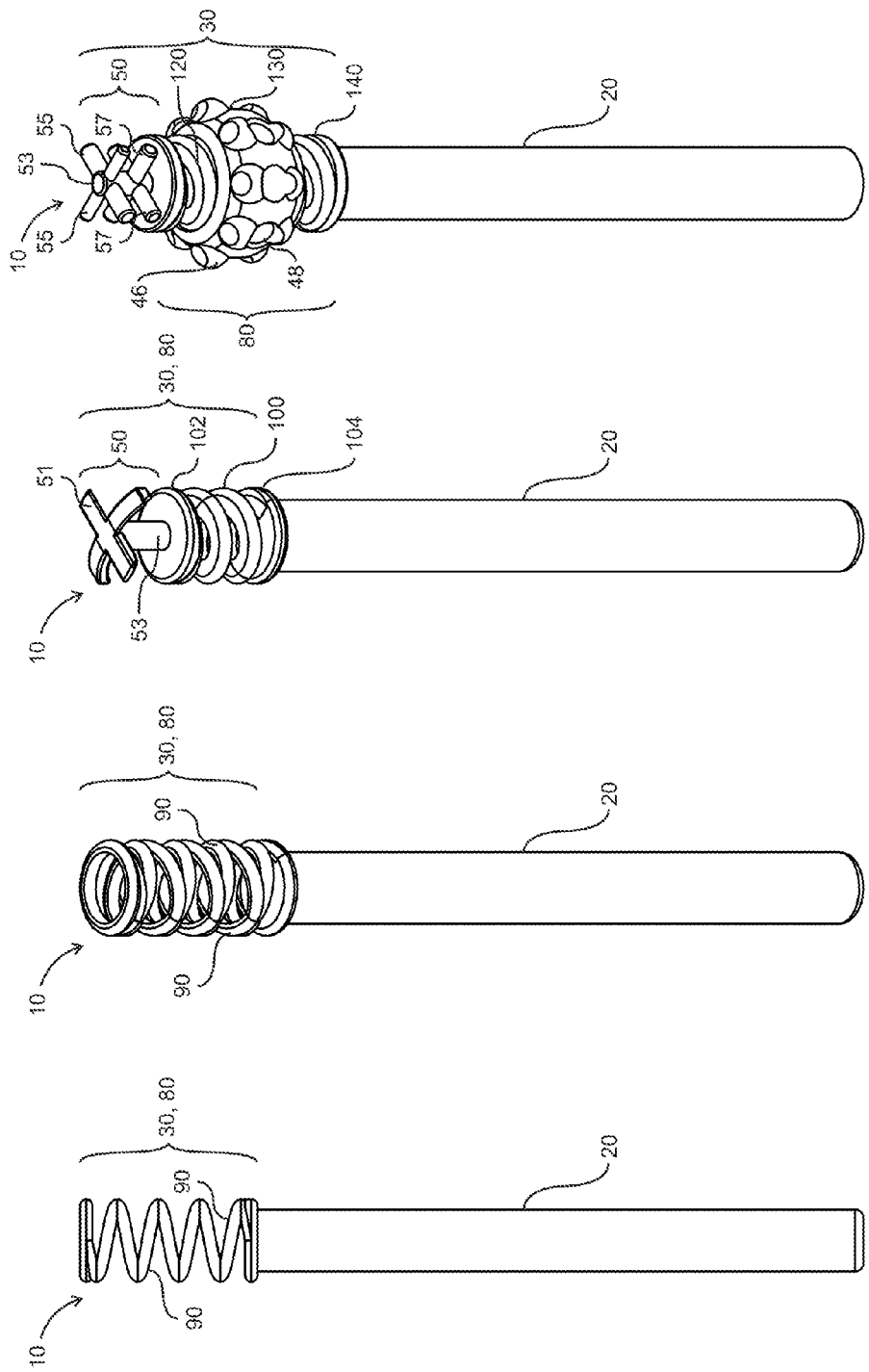

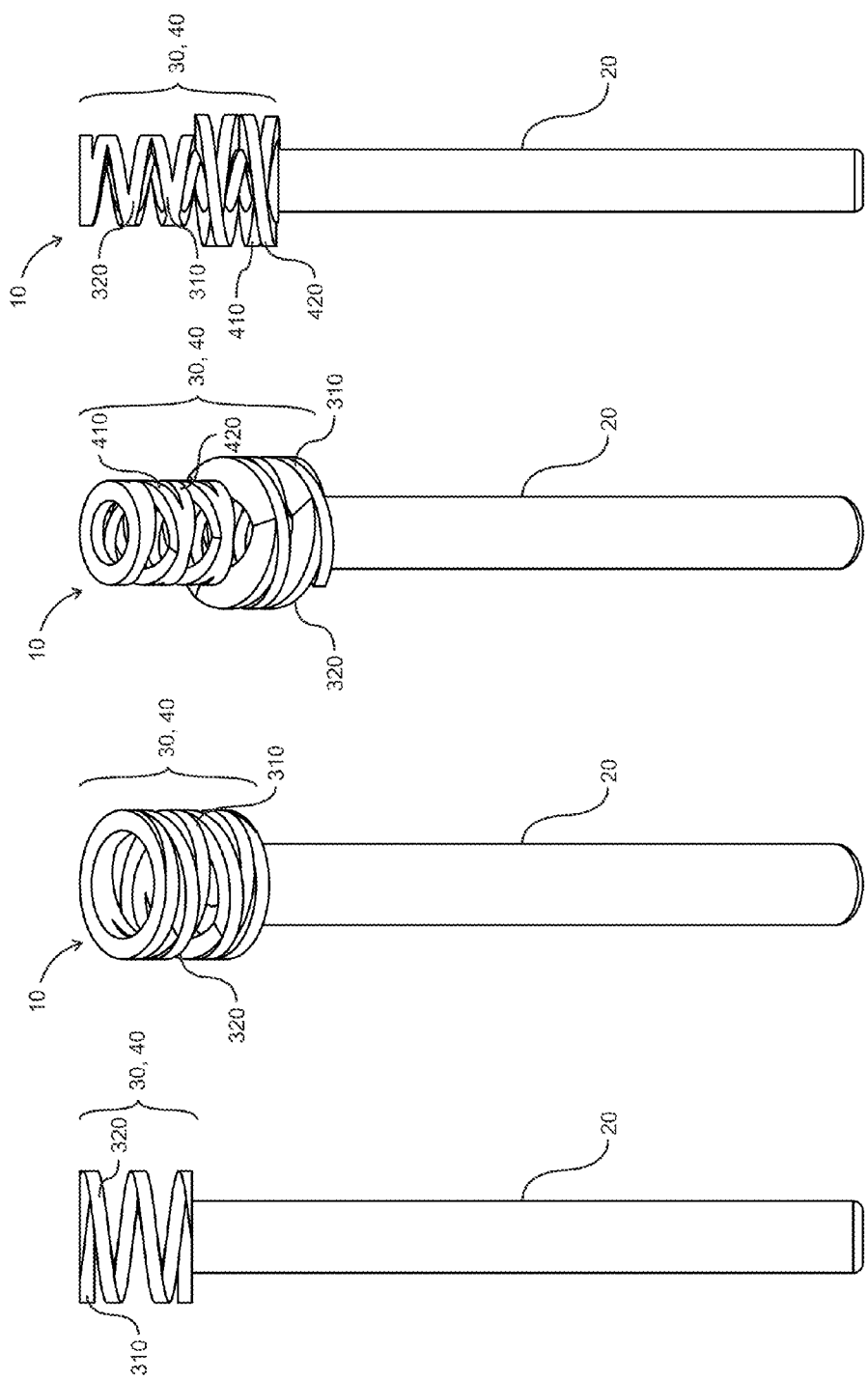

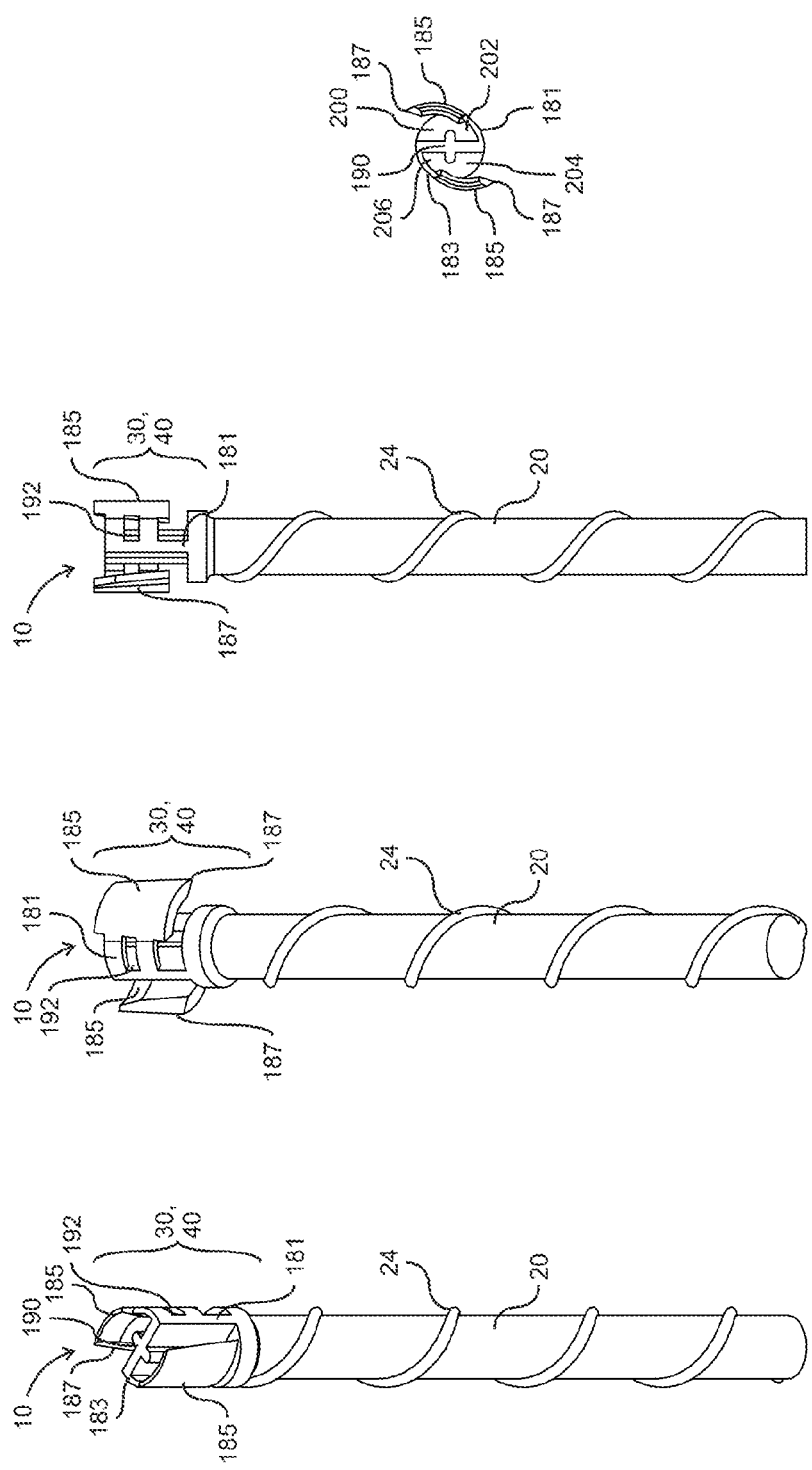

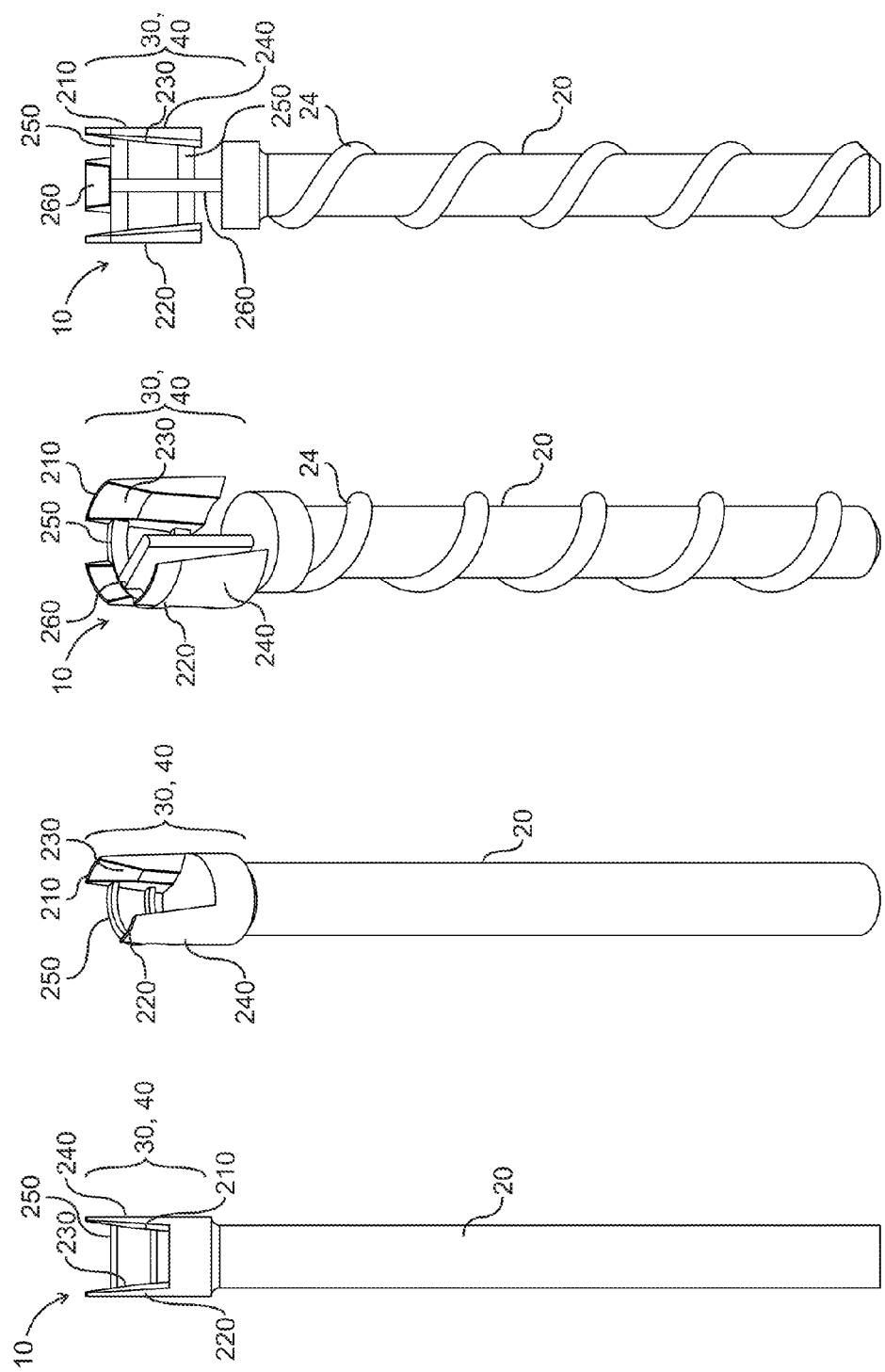

DEVICE AND METHOD FOR REMOVING EARWAX

CROSS-REFERENCE TO RELATED APPLICATIONS

This application is a continuation of U.S. application Ser. No. 14/329,700, filed on Jul. 11, 2014, which is a continuation of U.S. application Ser. No. 13/926,381, filed Jun. 25, 2013, which is a divisional of U.S. application Ser. No. 13/111,240, filed on May 19, 2011, the contents of each are incorporated by reference in their entireties.

BACKGROUND OF THE INVENTION

Field of the Invention

This invention relates to a device and method for removing earwax.

Description of Related Art

Devices for the extraction of earwax are generally known in the art. For example, U.S. Pat. No. 3,923,061 discloses a body with a padding mounted at one end of a shaft, wherein the padding has multiple grooves formed spirally in the body around the axis of the shaft. This design is disadvantageous because the body has narrow grooves that collect a small fraction of the superficial wax in an ear canal. Further, these general swab-type devices pack dense wax down into the ear canal generating a bolus of deep, chronic wax against the eardrum.

Similarly, U.S. Pat. No. 1,450,612 describes an earwax removal device comprising an ear manipulator mounted at one end of a shaft, wherein the outer surface of the manipulator is covered with a series of radially disposed soft fins, which serve to brush the passage in the ear when inserted therein, and twisted or rotated. The ear manipulator has a pointed end to aid the removal of the waxy deposit in the external auditory canal. Again the solid head tends to bludgeon wax medially. Furthermore, the blind manipulation of small tool tips can often result in damage to the delicate canal skin-tympanic membrane surface interface.

Techniques of wax removal known in the art fail to penetrate into hard, dry impacted wax for effective extraction. The known devices for removal by experts under direct visualization, e.g. metal curettes and picks, tend to stir and particulate the material, disengaging it piecemeal from the mass and often cause canal skin injury. Present rotating devices may engage soft wax on walls but do poorly with more solid accumulations, are readily misdirected hazardously, and can be dangerous near the eardrum. Known irrigation techniques are often performed blindly, can be cumbersome in many settings, and do not detach wax from skin. Residual wet wax can be a nidus for infection. Poorly performed irrigation results in vertigo by stimulating the posterior semicircular canal. Likewise, wax softeners may aid in extraction but do not extract.

More efficient and effective devices and methods for removing earwax are needed. For example, wax removal devices with structural variations that provide multiple methods of extracting different forms of wax are needed. Thus, an objective of the present invention is to provide a wax removal device that has varying tip and body structures that allow removal of wax in different manners simultaneously. Another object of the invention is to provide wax removal devices with varying body structures incorporating at least one channel within the body to effectively collect wax, steer the wax laterally out of the canal, and actively prevent impaction of wax often caused by the use of present devices. Yet another object of the invention is to provide devices with various compressible and extension structures to effectively engage and dislodge wax and minimize the risk of damage by overly forceful insertions. Also, more anatomically correct wax removal devices are needed to better conform to an ear canal to ensure that the surface contacts are flush with the skin and eardrum to avoid the damage that may occur when small tools are inserted blindly in uncontrolled directions. Canal-fitted tools can more effectively remove the wax in bulk. Improved tools can bore, grind and mince wax in the course of collection. With these goals in mind, the inventor has created an improved wax removal device and method having the aforementioned desired qualities.

BRIEF SUMMARY OF THE INVENTION

The present invention describes an earwax removal device comprising a shaft having a longitudinal axis and an earwax-extracting member. The earwax-extracting member can include a body portion and a tip portion, the body portion having a first end and a second end, the first end and the second end of the body portion located opposite each other, the tip portion located at the first end of the body portion, the shaft connected to the second end of the body portion. The shaft and earwax-extracting member can be several connected components or one integrated component. The body portion can include a guard member to protect the ear from insertion of the device.

The body portion can have varying widths. In some embodiments, an opening is formed in the tip portion and a hole is formed in at least one of the recesses of the body portion such that a tunnel is formed inside the earwax-extracting member.

In one embodiment, the body portion has multiple protrusions and recesses formed on the body portion. The tip portion can also comprise multiple protrusions.

In another embodiment, the body portion comprises multiple bristles protruding substantially perpendicular to the longitudinal axis of the shaft and the tip portion comprises a cone-shaped spiral. In another embodiment, the tip portion comprises multiple elongated protrusions extending substantially parallel to the longitudinal axis of the shaft.

Another earwax removal device described herein comprises a shaft having a longitudinal axis and an earwax-extracting member comprising a flexible body, the flexible body connected to an end of the shaft, the flexible body capable of contracting and extending in a direction substantially parallel to the longitudinal axis of the shaft. The flexible body can comprise a plurality of rings, the rings connected and stacked in a zigzag manner. In one embodiment, the flexible body comprises a spiral member, the spiral member having a first end and a second end, the first end and the second end of the spiral member located opposite each other, the earwax-extracting member further comprising a tip portion, the tip portion comprising a cross-shaped element and a bar, the bar connected to the cross-shaped element and extending from the first end of the spiral member in a direction substantially parallel to the longitudinal axis of the shaft, the shaft connected to the second end of the spiral member.

In another embodiment, the flexible body can comprise a first spiral section, an intermediate section, and a second spiral section, the second spiral section connected to the shaft, the intermediate section connected to the first spiral section and to the second spiral section and located between the first spiral section and the second spiral section, the intermediate section having a width perpendicular to the longitudinal axis of the shaft, the first spiral section having a width perpendicular to the longitudinal axis of the shaft, the second spiral section having a width perpendicular to the longitudinal axis of the shaft, the width of the intermediate section being larger than the width of the first spiral section and larger than the width of the second spiral section. This embodiment can also have a tip portion comprising a vertical bar, a first pair of horizontal bars and a second pair of horizontal bars, the vertical bar extending from the first spiral section in a direction substantially parallel to the longitudinal axis of the shaft, the first pair of horizontal bars extending from a first location of the vertical bar such that the first pair of horizontal bars cross each other, the second pair of horizontal bars extending from a second location of the vertical bar such that the second pair of horizontal bars cross each other, the first location of the vertical bar more distant from the first spiral section than the second location of the vertical bar, the first pair of horizontal bars and the second pair of horizontal bars substantially perpendicular to the longitudinal axis of the shaft.

In yet another embodiment, the earwax-extracting member can comprise a central rod having a first end and a second end, the second end connected to an end of the shaft, the central rod extending in a direction substantially parallel to the longitudinal axis of the shaft and a helical ridge member extending about the central rod. The helical ridge member can further have at least one notch therethrough.

In another embodiment, the body portion of the device can comprise a set of two interconnected and overlapping helical structures. The body portion can further have a second set of two interconnected and overlapping helical structures connected to the first set of two interconnected and overlapping helical structures, both sets having varying widths.

In yet another embodiment, the body portion can comprise a curved elongated member extending substantially parallel to the longitudinal axis and forming an interior space and an elongated cross-bar member extending substantially parallel to the longitudinal axis within the interior space, wherein a first quadrant, a second quadrant, a third quadrant, and a fourth quadrant are formed between the curved elongated member and the elongated cross-bar. The quadrants can be open or closed along the length of the body. The body can further comprise a plurality of holes into a channel formed by a quadrant, each hole further comprising a projecting member capable of guiding earwax into the hole and into the channel.

In another embodiment, the curved elongated member can comprise a first flag member and a second flag member, said first flag member and said second flag member attached to a pair of opposing ends of said elongated cross-bar member.

Another embodiment of the device has a body portion having a first and second elongated member, each extending substantially parallel to the longitudinal axis, and each having a sloped interior surface and curved exterior surface.

A method for earwax removal is also described, generally comprising the steps of providing an embodiment of an earwax removal device described herein, inserting the earwax-extracting member of the earwax removal device into the ear canal, and pulling out the earwax-extracting member of the earwax removal device from the ear canal. Prior to pulling out the device, a step of rotating the earwax removal device while the earwax-extracting member of the earwax removal device is located in the ear canal can be included.

BRIEF DESCRIPTION OF THE SEVERAL VIEWS OF THE DRAWINGS

FIG. 1 illustrates an embodiment of a wax removal device having a body comprising multiple protrusions and recesses according to the present invention;

FIG. 2 illustrates an embodiment of a wax removal device having a body comprising multiple protrusions and recesses, and a tunnel therethrough, according to the present invention;

FIG. 3 illustrates an embodiment of a wax removal device having a body of varying widths and comprising multiple protrusions and recesses according to the present invention;

FIG. 4 illustrates an embodiment of a wax removal device having a body comprising multiple protrusions and recesses according to the present invention;

FIG. 10A illustrates an orthogonal view of an embodiment of a wax removal device having a ring structure according to the present invention;

FIG. 10B illustrates a perspective view of an embodiment of a wax removal device having a ring structure according to the present invention;

FIG. 11 illustrates an embodiment of a wax removal device having a spiral member and a cross-shaped tip according to the present invention;

FIG. 12 illustrates an embodiment of a wax removal device having a spiral member and intermediate section comprising protrusions and recesses according to the present invention;

FIG. 16A illustrates a side view of an embodiment of a wax removal device having overlapping and interconnecting helical structures according to the present invention;

FIG. 16B illustrates a perspective view of an embodiment of a wax removal device having overlapping and interconnecting helical structures according to the present invention;

FIG. 17A illustrates a perspective view of an embodiment of a wax removal device having two sets of overlapping and interconnecting helical structures according to the present invention;

FIG. 17B illustrates a side view of an embodiment of a wax removal device having two sets of overlapping and interconnecting helical structures according to the present invention;

FIG. 21A illustrates a perspective view of an embodiment of a wax removal device having flag members according to the present invention;

FIG. 21B illustrates a perspective side view of an embodiment of a wax removal device having flag members according to the present invention;

FIG. 21C illustrates a side view of an embodiment of a wax removal device having flag members according to the present invention;

FIG. 21D illustrates a top view of an embodiment of a wax removal device having flag members according to the present invention;

FIG. 22A illustrates a side view of an embodiment of a wax removal device having a shovel-type elongated member according to the present invention;

FIG. 22B illustrates a perspective view of an embodiment of a wax removal device having a shovel-type elongated member according to the present invention;

FIG. 23A illustrates a perspective view of an embodiment of a wax removal device having a shovel-type elongated member according to the present invention;

FIG. 23B illustrates a side view of an embodiment of a wax removal device having a shovel-type elongated member according to the present invention.

DETAILED DESCRIPTION OF THE INVENTION

Figure 7:
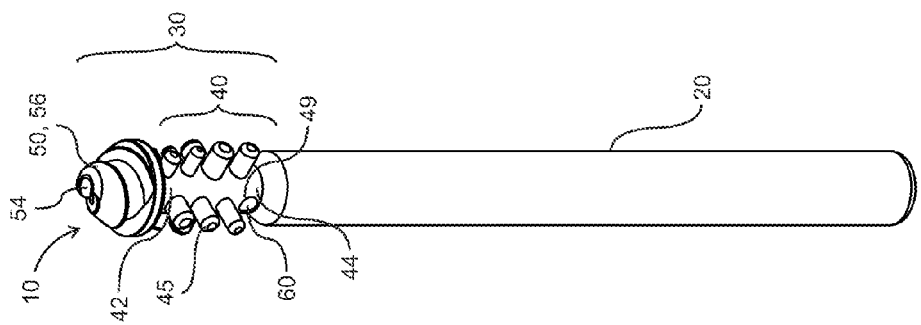
FIG. 7 illustrates an embodiment of a wax removal device having bristles, a cone tip, and a tunnel through the body according to the present invention.

The detailed description set forth below in connection with the appended drawings is intended to provide example embodiments of the present invention and is not intended to represent the only forms in which the invention may be constructed or utilized. The description sets forth the functions and the sequences of steps for constructing and operating the invention. However, it is to be understood that the same or equivalent functions and sequences may be accomplished by different embodiments that are also intended to be encompassed within the spirit and scope of the invention.

Some embodiments of the invention will be described in detail with reference to FIGS. 1-24. Additional embodiments, features, and/or advantages of the invention will become apparent from the description or may be learned by practicing the invention. The drawings in the figures are not necessarily drawn to scale and have like numerals referring to like features through both the drawings and the description.

FIGS. 1 through 24 illustrate embodiments of earwax removal devices and methods for removing earwax. An earwax removal device 10 generally comprises a shaft 20 having a longitudinal axis and an earwax-extracting member 30. The earwax-extracting member 30 and shaft 20 can be separate and removably connected, or can be made as one integrated structure. The two-piece configuration can include elements that screw together via a thread-fit, friction fit, snap-fit or any other suitable type of attachment. This configuration also allows one to choose which embodiment of the earwax-extracting member 30 to use based on the desired earwax removal capabilities such that the earwax-extracting members 30 are interchangeable.

The components of the device 10 may be made of plastic, rubber, metal, or another suitable material as required for desired control and flexion. Additionally, the device 10 can be comprised of a single, solid material or can have a core material with an outer shell, e.g. a wire covered by a molded plastic that has the appropriate structure. The device 10 and its components are intended to be either disposable or reusable. The device 10 can also be made of a material suitable for various methods of sterilization, including irradiation.

The shaft 20 may be of varying lengths and widths. The shaft 20 can be manually rotated by the user or can incorporate a motor-driven shaft 20 that provides rotation. A typical length range can be two to three inches, but longer or shorter lengths may be utilized depending on the desired amount of control. The width of the shaft 20 can be similar to that of the ear canal, about six to seven millimeters, particularly when the shaft 20 and earwax-extracting member 30 form a single structure. The shaft 20 can also include gripping surface 24, such as a flange design, etching, spiral ridging or a coarse surface, to improve handling. The shaft 20 can also include a handle 26 in any suitable form for improved gripping.

The design of the shaft 20 of the device 10 generally remains the same while the earwax-extracting member 30 can have significantly different structures. However, each embodiment of the present invention may have several common properties. Unless otherwise specified, each embodiment can include a conical surface configuration or conical configuration of members at the tip portion 50 of the device 10 to meet flush with the tympanic membrane. Each device 10 can have a soft widening of the body portion 40 or increase in the height of the active surface members, which create a gradual widening of the wax removal tip as the external auditory canal widens. Further, each device 10 can include an opening 54 in the tip portion 50 that leads to a channel through which wax is actively driven or channeled by the pressure of device 10 insertion and rotation. The body portion 40 of the earwax-extracting member 30 can include an exit hole 49 to exhaust wax under pressure in the device body closer to the tip. The device 10 can be comprised of a flexible material such that the body of the earwax-extracting member 30 can compress and expand to dislodge engaged wax. Use of a softer material, such as soft plastic or rubber, can allow for a tight fit of the earwax-extracting member 30 against the ear canal skin, thereby enhancing functionality. Ear wax removing tips with soft core or compressible design will self-guide through the external auditory canal tortuosities and compress to minimize the risk of damage during blind insertion. In addition, the earwax-extracting members 30 that anatomically fit the external auditory canal can remove the wax bolus as a single collection.

The typical human ear canal is about five to six millimeters across in the bony portion near the tympanic membrane and about eight to ten millimeters wide ear the lateral, cartilaginous region. The canal length, about two to three centimeters long, defines the maximum depth of penetration of the earwax-extracting member 30. Various widths permit the device 10 to adapt to individual variations in the human ear canal. Anatomically correct wax removal devices better conform to an ear canal to ensure that the surface contacts are flush with the skin and eardrum to avoid damage that may occur when small tools are inserted blindly in uncontrolled directions. Also, the canal-fitted tools can more effectively remove the wax in bulk. Other configurations can be determined for appropriate animals.

The device 10 can have internal safety guards to control the depth at which the device 10 is inserted in the ear canal. For example, each device 10 can include a guard member 70, such as a ring or coil, or another suitable sharp local flaring at about five to seven millimeters from the tip portion 50 or end of the earwax-extracting member 30. The guard member 70 is intended to limit the extent of tip penetration at the narrowing of the canal known as the "bony-cartilaginous junction."

Additional rings or flares along the earwax-extracting member's body can be included to control the width of the body and limit penetration in the ear from the conchal bowl region into the external auditory canal itself. They can be used to adjust the exposure of the functional elements, such as bristles 45, to the canal skin surface. Such embodiments can comprise three extension members distributed about the body portion 40 and tip portion 50 of the device 10. A first extension member is located along the perimeter of the tip portion 50, a second extension member is located at the junction of the upper section 41 and lower section 43 of the body portion 40, and a third extension member is located at an end of the wax extracting member 30 closest to the shaft 20 of the device 10. The extension members may be in the shape of solid rings or coils and can be used to control the depth to which the earwax-extracting member 30 can be inserted in the ear canal. Section dividing rings or coils can enhance device 10 rotation through canal curvatures.

As discussed above, the earwax-extracting member 30 may have variations in dimensions and configurations. For example, a straight, wide cylindrical design can contact the ear canal walls more evenly and draw in softer wax as it rotates. A conical design that tapers toward the tip may bore into a harder wax plug, intending to engage the plug and extract it entirely. A narrow cylindrical design may bore smaller holes into a large solid wax accumulation, which may facilitate removal with a second extraction technique. All surfaces of the earwax-extracting members 30 can be textured or etched to increase hold of the wax onto the device 10. A wide base, with or without a narrower tip segment, is a safety control that can limit penetration of the wax removing tip.

The earwax-extracting member 30 may vary in sharpness and hardness. Soft wax would be safely and effectively removed with soft outer edges whereas harder wax may warrant sharper, blade-like edges that cut into the wax. The earwax-extracting member 30 may terminate with or without a tip such that it can have a flat end or have a gentle, conical rise that can engage wax near the tip. The conical design may come to a point or have a blunt end. A flat, umbrella-style cover may be added to the end of the earwax-extracting member 30 to minimize the risk of damage to the eardrum. The umbrella-style cover may have an added coating or surface material, such as foam or cotton to further prevent potential damage to the eardrum. The ear-extracting member in all embodiments can be made of a soft, malleable plastic, rubber, or other suitable material to conform to the anatomical shape of the ear canal.

All embodiments of the earwax-extracting member 30 can flex and can be compressible in a direction along the longitudinal axis of the shaft 20 of the device 10. The range of compressibility is approximately one millimeter to four millimeters. Embodiments using firmer plastics generally compress when coil or spring segments are utilized. Embodiments using softer materials can vary in the amount of compressibility, depending on the structure of the earwax-extracting member 30. The various compressible and extension structures of the earwax-extracting member 30 effectively engage and dislodge wax while minimizing the risk of damage that can be caused by overly forceful insertions.

The earwax-extracting member 30 can have a hollow core to admit and collect wax, as well as an opening 54 at the tip portion 50, to core into impacted wax. The openings in the earwax-extracting member 30 can lead to at least one channel within the body to effectively collect wax, steer the wax laterally out of the canal, and actively prevent impaction of wax. In other embodiments, the body portion 40 may be comprised of a harder material to scrape out harder wax in the ear canal. In addition, the hollow interior may be filled with a wire mesh that aids in grating wax, or a cutting blade(s) to cut canal hair.

Several non-limiting specific embodiments of the device 10 having various earwax-extracting members 30 are described below. The scope of the invention shall not be limited to the following examples or their headings.

Embodiments of the Present Invention Having a "Club" Design

As shown in FIGS. 1-4, the "club" embodiment of the device 10 comprises an earwax-extracting member 30 having an irregular surface with a bump and trough pattern. Some troughs may open into an optional wax channel(s) through the earwax-extracting member 30. An optional central channel network may steer compressed wax laterally through the device 10. The embodiment can be made in a soft material that could allow "sponging" of wax into its center.

As illustrated in FIG. 1, the earwax removal device 10 comprises a shaft 20 having a longitudinal axis and an earwax-extracting member 30. As a non-limiting example, the earwax-extracting member 30 can have a length in a range of between about ten to twelve millimeters. The earwax-extracting member 30 has a body portion 40 having a first end 42 and a second end 44, the first end 42 and the second end 44 of the body portion 40 located opposite each other. The earwax-extracting member 30 also has a tip portion 50 located at the first end 42 of the body portion 40. The shaft 20 is connected to the second end 44 of the body portion 40.

Multiple protrusions 46 and multiple recesses 48 are formed on the surface of the body portion 40 and multiple protrusions 52 are formed on the tip portion 50. FIG. 2 illustrates that the protrusions 46 of the body portion 40 and the recesses 48 of the body portion 40 can be arranged alternately and can be curved or substantially round in shape. Also, as shown in FIG. 1, the multiple protrusions 46 of the body portion 40 can vary in size, a first group of protrusions 46A being smaller in size than a second group of protrusions 46B. The differently sized protrusions 46 can create an irregular or irregularly, irregular surface. The protrusions 46 can also be coupled with troughs or deep-set entrances into a tunnel 60 that is formed inside the earwax-extracting member 30.

The widths of the body portion 40 at two different distances from the second end 44 of the body portion 40 are different from each other. The varying widths allow the device 10 to better fit within the ear canal. For example, as shown in FIG. 3, the body portion 40 can be divided among an upper section 41 and a lower section 43. In such embodiments, the width of the lower section 43 can be larger than the width of the upper section 41 to better fit the ear canal. The device 10 can include coil or ring connections between segments to allow rotation and flexion between medial and lateral components.

To prevent damage to the eardrum, the tip portion 50 can be slanted in a conical manner such that an angle between a tangent plane to a central surface of one of the protrusions 52 of the tip portion 50 and a horizontal plane perpendicular to the longitudinal axis of the shaft 20 is approximately 15° or less. To further prevent damage to the eardrum, a guard member 70, such as a ring or other suitable extending structure, can surround the body portion 40 at the second end 44 of the body portion 40.

Alternatively, a safety mechanism can be used at three junctions of the ear-extracting member. For example a safety mechanism can include three extension members, a first extension member 32 surrounding the perimeter of the tip portion 50, a second extension member 34 surrounding the perimeter of the body portion 40 and located between the upper section 41 and the lower section 43, and a third extension member 36 surrounding the perimeter of the body portion 40 and located proximate to the second end 44 of the body portion 40. The first through third extension member can increase in size to anatomically correspond with the ear.

In some embodiments, shown in FIG. 2, the earwax-extracting member 30 can include a channel therethrough. In such embodiments, an opening 54 is formed in the tip portion 50 where wax can enter the device 10 into a tunnel 60 that is formed inside the earwax-extracting member 30. Earwax can also enter into the tunnel 60 through troughs or deep-set entrances coupled with protrusions 46 on the body. The wax can subsequently exit through an exhaust port or hole 49 in at least one of the recesses 48 of the body portion 40.

Embodiments of the Present Invention Having a "Bristle" Design

Figure 6:
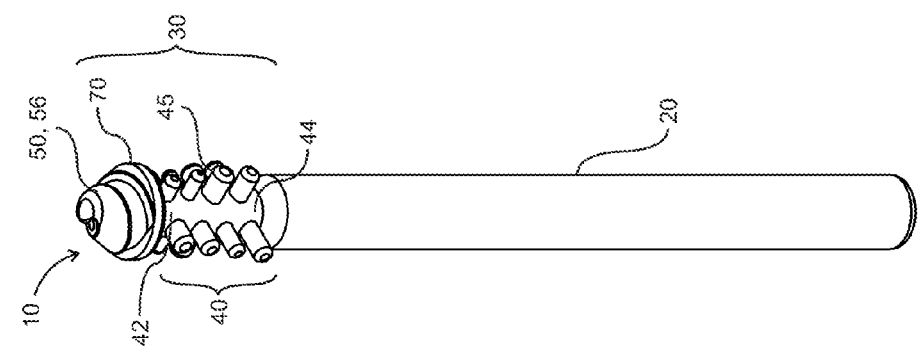
FIG. 6 illustrates an embodiment of a wax removal device having bristles and a cone tip according to the present invention.
Figure 5:
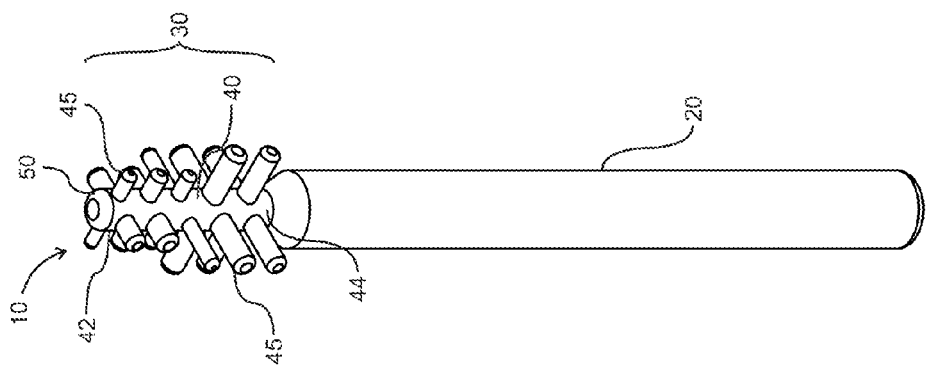
FIG. 5 illustrates an embodiment of a wax removal device having bristles according to the present invention.

FIGS. 5 through 9 illustrate several different embodiments of the device 10 having bristles 45. Varying the bristle width and length as shown in FIG. 5 will allow for controlled wax removal while the direction of the bristles 45 will allow for collection of wax in a particular direction. The earwax-extracting member 30 of this embodiment has a body portion 40 comprising multiple bristles 45 protruding substantially perpendicular to the longitudinal axis of the shaft 20. The bristles 45 can be in a configuration that is adapted to fit an eardrum-canal skin envelope. As shown in FIGS. 5-7, the bristles 45 can be substantially cylindrical in shape and vary in size. The bristles 45 allow for effective dislodging and removal of wax upon rotation of the device 10.

In an alternative embodiment shown in FIG. 6, the tip portion 50 of the earwax-extracting member 30 can include a cone-shaped spiral 56 to bore into wax. In another alternate embodiment shown in FIG. 7, an opening 54 is formed in the tip portion 50, a hole 49 is formed in the body portion 40, and a tunnel 60 is formed inside the earwax-extracting member 30 such that the opening 54 of the tip portion 50 and the hole 49 of the body portion 40 are connected to the tunnel 60. Wax can thereby enter the device 10 through the opening 54 and exit the device 10 through the hole 49 in the wax-extracting member 30.

Figure 9:
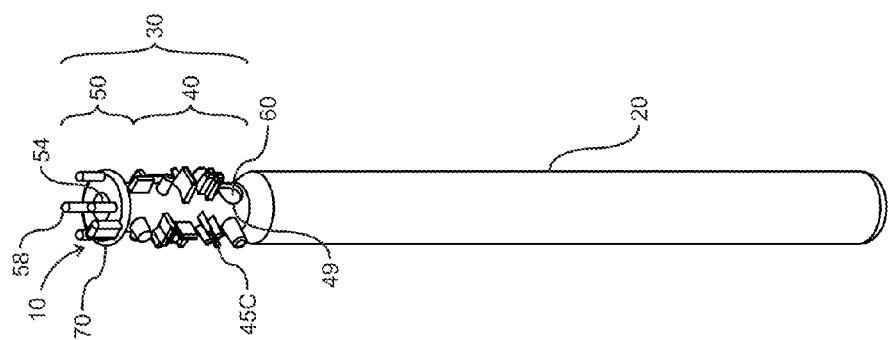
FIG. 9 illustrates a perspective view of an embodiment of a wax removal device having bristles, a tip having protrusions, and a tunnel through the body according to the present invention.
Figure 8B:
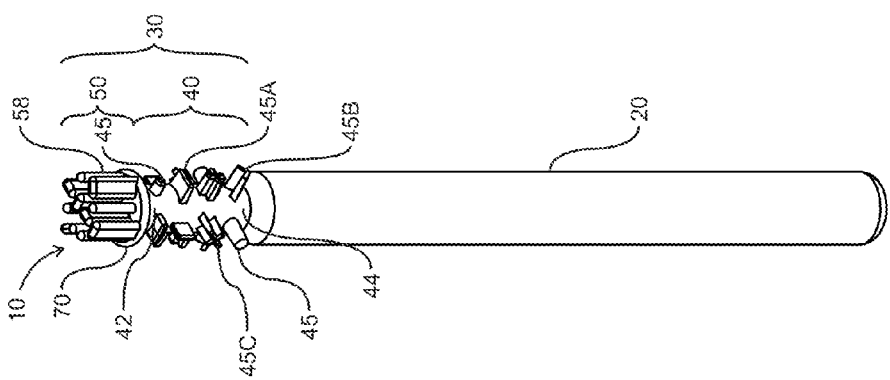
FIG. 8B illustrates a perspective view of an embodiment of a wax removal device having bristles and a tip having protrusions according to the present invention.
Figure 8A:
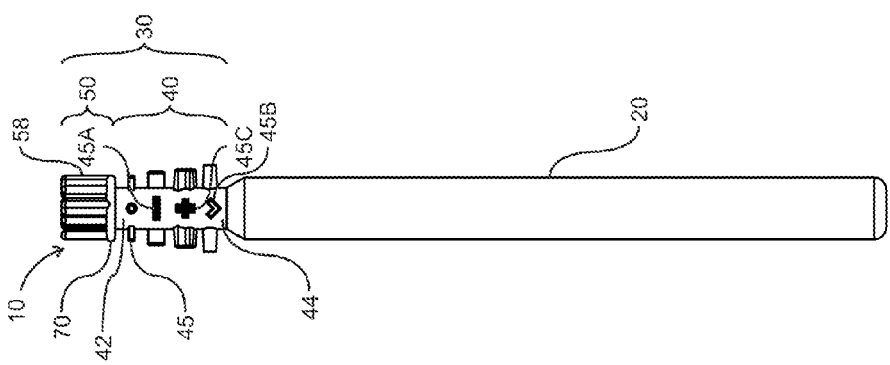
FIG. 8A illustrates an orthogonal view of an embodiment of a wax removal device having bristles and a tip having protrusions according to the present invention.

In yet another alternate embodiment shown in FIGS. 8A and 8B, the tip portion 50 can comprise multiple elongated protrusions 58 extending substantially parallel to the longitudinal axis of the shaft 20 to further dislodge and remove wax. Also shown in FIGS. 8A and 8B, the bristles 45 of the body portion 40 can have different sizes and shapes, including a rectangular 45A, V 45B, and plus-sign (+) 45C shape. As shown in FIG. 9, this embodiment can also have an opening 54 in the tip portion 50 connected to a tunnel 60 through the body portion 40 and exhaust hole 49 in the body portion 40 for wax removal.

Embodiments of the Present Invention Having a "Coil" Design

The device 10 having a flexible coil-like earwax-extracting member 30 is shown in FIGS. 10 through 12. As shown in FIGS. 10-12, the earwax-extracting member 30 can comprise a flexible body 80 connected to an end of the shaft 20 and capable of contracting and extending in a direction substantially parallel to the longitudinal axis of the shaft 20. When this embodiment of the device 10 is used, the inward pressure on the spring member allows the device 10 to core into wax, after which the spring nature can tighten the spring member around the wax as extraction occurs. By virtue of its spring action, repeat tugs on this device 10 can dislodge a bolus from canal skin. A spring member or multiple spring members at the base or junctions of the ear-extracting member 30 of the device 10 can reduce the risk of damage from overly forceful insertion.

The flexible body 80 can be comprised of a plurality of rings 90, the rings 90 connected and stacked in a zigzag manner as shown in FIGS. 10A and 10B. The rings 90 can have varying widths that are perpendicular to the longitudinal axis of the shaft 20. In another embodiment shown in FIG. 11, the flexible body 80 comprises a spiral member 100 having a first end 102 and a second end 104. The first end 102 and the second end 104 of the spiral member 100 are located opposite each other. The earwax-extracting member 30 further comprises a tip portion 50 having a cross-shaped element 51 and a bar 53. The bar 53 of the tip portion 50 is connected to the cross-shaped element 51 and extending from the first end 102 of the spiral member 100 and the shaft 20 is connected to the second end 104 of the spiral member 100. In this embodiment, the tip portion 50 can penetrate wax a few millimeters to anchor to the bolus, and even the spiral member 100 can catch more superficial portion of a cerumen bolus. The spring action of the spiral member 100 allows intermittent tugs to dislodge the bolus.

In yet another embodiment shown in FIG. 12, the flexible body 80 comprises a first spiral section 120, an intermediate section 130, and a second spiral section 140. The second spiral section 140 is connected to the shaft 20, the intermediate section 130 is located between the first spiral section 120 and the second spiral section 140. The intermediate section 130 is similar to the "club" embodiment of the device 10 in that it can include protrusions 46 and recesses 48 to better facilitate wax removal. In addition, the earwax-extracting member 30 can include a tip portion 50 having a vertical bar 53. A first pair 55 and a second pair 57 of horizontal intersecting bars can be attached to the vertical bar 53 to also better remove wax.

Embodiments of the Present Invention Having a "Screw" Design

Several screw-type embodiments of the device 10 are illustrated in FIGS. 13-17B.

Figure 13A:
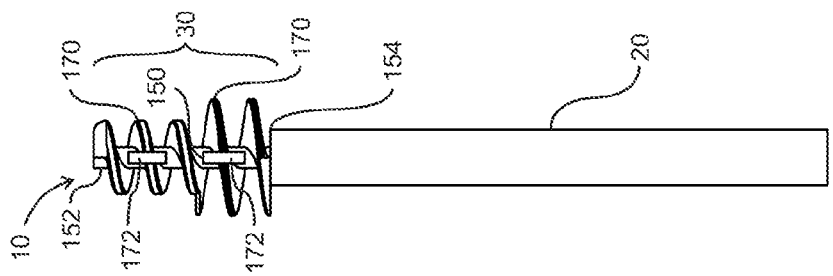
FIG. 13A illustrates a perspective view of an embodiment of a wax removal device having a helical ridge member according to the present invention.
Figure 13B:
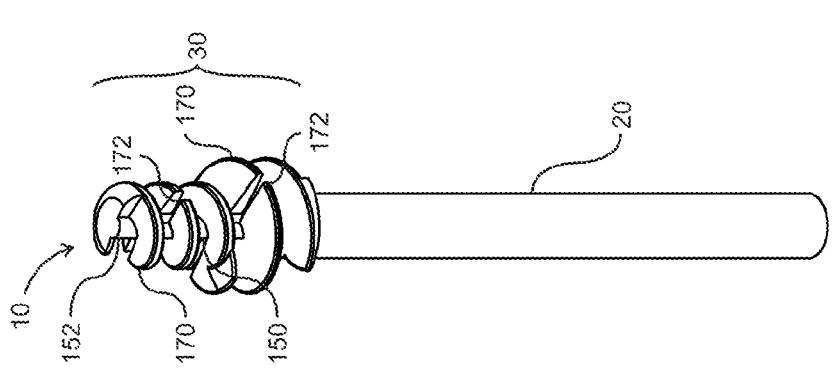
FIG. 13B illustrates a side view of an embodiment of a wax removal device having a helical ridge member according to the present invention.

For example, as illustrated in FIGS. 13A and 13B, the earwax-extracting member 30 of this embodiment can comprise a central rod 150 and a helical ridge member 170 extending about the central rod 150. The earwax-extracting member 30 of this embodiment drives wax laterally as device 10 turns. This embodiment provides a mechanism for removing wax in which the wax is not simply bound to surface or within cavity but channeled by the force of insertion and turning into a lateral portion of the body, thereby promoting lateral excursion of wax. The screw configuration self-steers and seals along the canal walls during insertion.

Figure 14A:
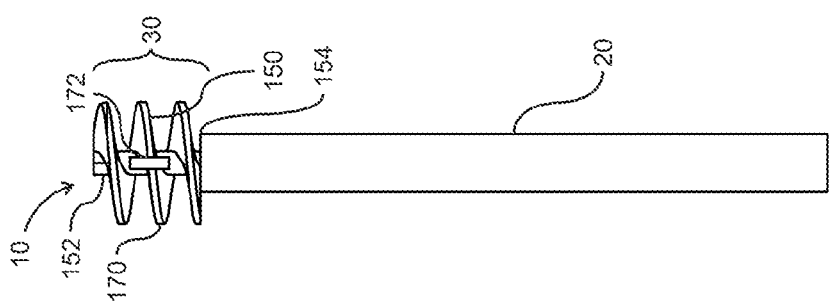
FIG. 14A illustrates a perspective view of an embodiment of a wax removal device having a helical ridge and varying widths according to the present invention.
Figure 14B:
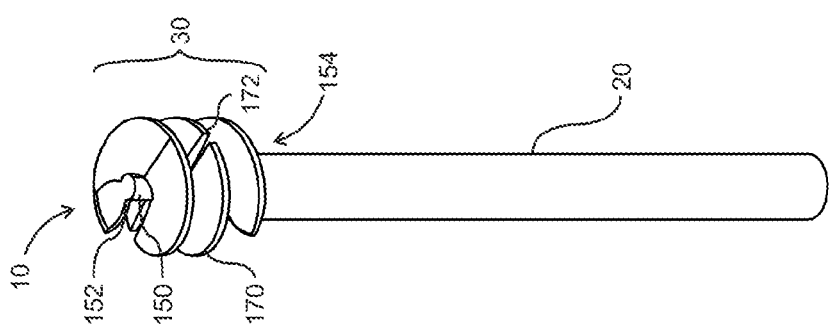
FIG. 14B illustrates a side view of an embodiment of a wax removal device having a helical ridge and varying widths according to the present invention.
Figure 15A:
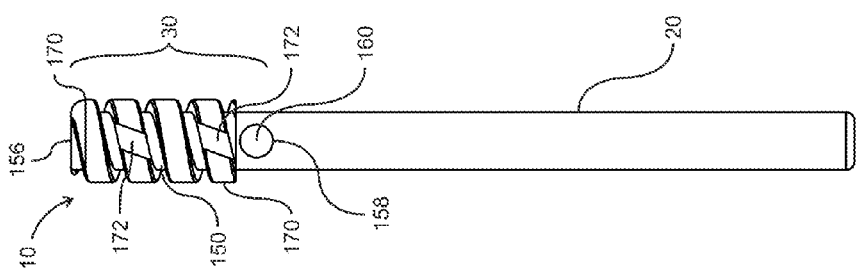
FIG. 15A illustrates a perspective view of an embodiment of a wax removal device having a helical ridge, and a tunnel therethrough, according to the present invention.
Figure 15B:
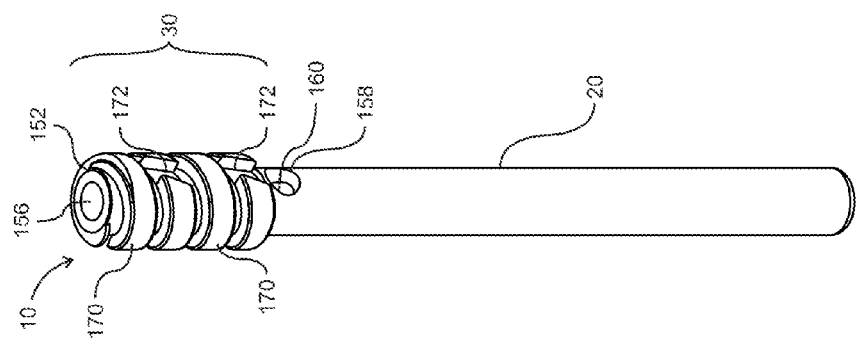
FIG. 15B illustrates a side view of an embodiment of a wax removal device having a helical ridge, and a tunnel therethrough, according to the present invention.

As shown in FIGS. 14A and 14B, the helical ridge member 170 can have varying widths to accommodate and better fit the anatomical structure of the ear canal. As shown in FIGS. 13A-15B, the earwax-extracting member 30 can also include one or more notches 172 that grind the engaged wax within channel of the helical ridge member 170. Like the other embodiments, an opening 156 can be formed at the first end 152 of the central rod 150, leading to a tunnel 160 formed therein to collect wax, as shown in FIGS. 15A and 15B. An exit hole 158 at a second end 154 of the central rod 150 can be used to empty the wax from the tunnel 160.

In another embodiment of the earwax-extracting member 30, illustrated in FIGS. 16A and 16B, the body portion 40 can be comprised of a set of two interconnected and overlapping helical structures 310, 320. Alternatively, as shown in FIGS. 17A and 17B, the body portion 40 can have a second set of interconnected and overlapping helical structures 410, 420, each set having a different width to better fit the ear canal and extract wax out of the ear when the device 10 is rotated.

Embodiments of the Present Invention Having a "Multi-Channel" Design

Figure 18A:
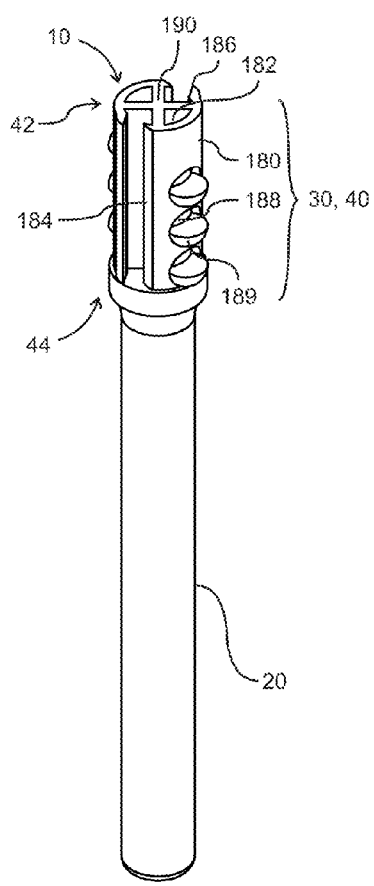
FIG. 18A illustrates a perspective view of an embodiment of a wax removal device having channels and cutting structures according to the present invention.
Figure 18B:
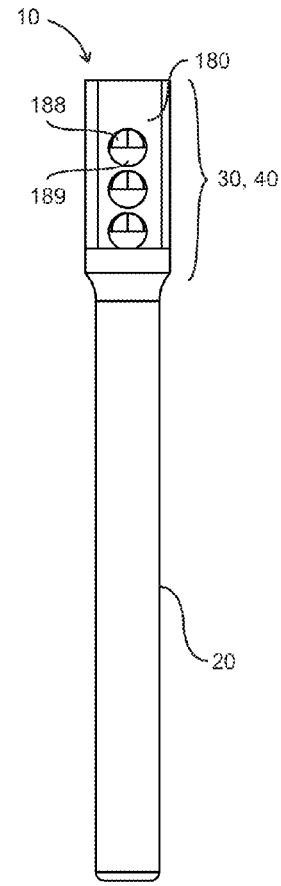
FIG. 18B illustrates a side view of an embodiment of a wax removal device having channels and cutting structures according to the present invention.
Figure 18C:
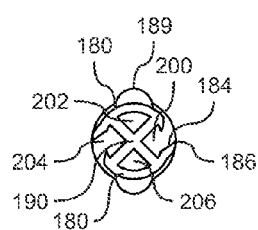
FIG. 18C illustrates a top view of an embodiment of a wax removal device having channels and cutting structures according to the present invention.
Figure 20:
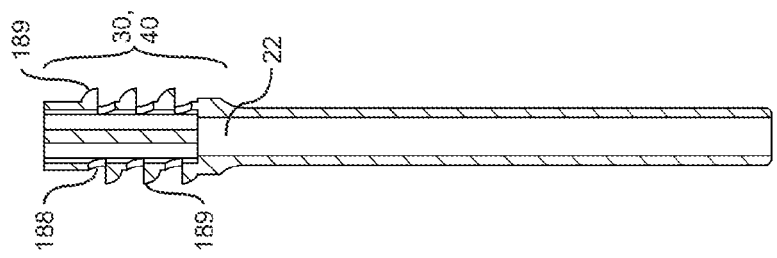
FIG. 20 illustrates a cross-sectional view of an embodiment of a wax removal device having channels, cutting structures, and a tunnel therethrough, according to the present invention.
Figure 19C:
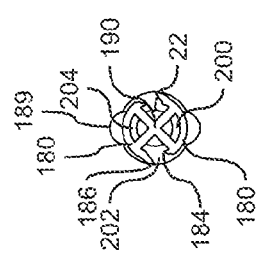
FIG. 19C illustrates a top view of an embodiment of a wax removal device having channels, cutting structures, and a tunnel therethrough, according to the present invention.
Figure 19B:
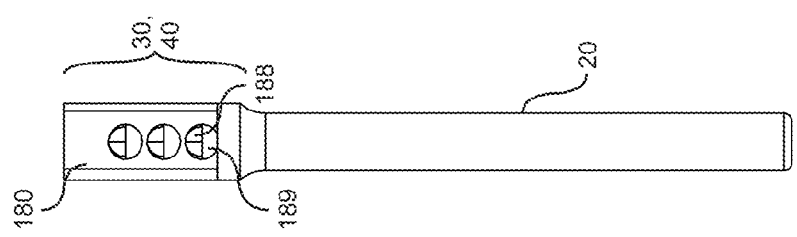
FIG. 19B illustrates a side view of an embodiment of a wax removal device having channels, cutting structures, and a tunnel therethrough, according to the present invention.
Figure 19A:
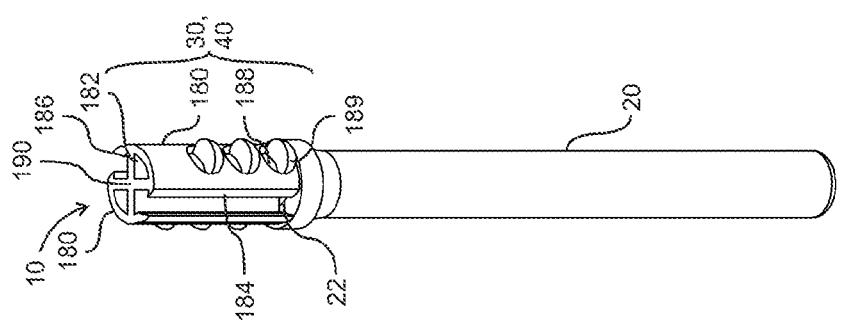
FIG. 19A illustrates a perspective view of an embodiment of a wax removal device having channels, cutting structures, and a tunnel therethrough, according to the present invention.

The device 10 having a multi-channel design is shown in FIGS. 18-20. This design resembles a "potato masher" in that the tip portion 50 where the channels meet the wax can break up the wax and admit the wax into the channels. This design also has resembles a "potato peeler" in that the side slits in the channels can cut wax and admit wax into the channels along the sides of the earwax-extracting member 30. Lastly, this embodiment resembles a "cheese grater" in that the projecting members can engage wax in the direction of the projecting members as the device 10 moves in, out, or rotates. Each projecting member can be a turret to provide optional rotation of the projecting member.

As shown in FIGS. 18A-20, the earwax-extracting member 30 has a body portion 40 comprising a curved elongated member 180 extending substantially parallel to the longitudinal axis. The curved elongated member 180 forms an interior space 182 within it. An elongated cross-bar member 190 extending substantially parallel to the longitudinal axis is connected to the curved elongated member 180 within its interior space 182. A first 200, second 202, third 204, and fourth 206 channel are formed as a result of the connection between the curved elongated member 180 and elongated cross-bar 190. The tip of the earwax-extracting device 10 can thereby cut and collect wax into the four channels formed therein.

Further, as shown in FIGS. 18A-20, a slit 184 can be formed in a curved elongated member 180. The slit 184 can extend from the first end 42 to the second end 44 of the body portion 40 and can include a pointed lip 186 along a longitudinal edge of the slit 184 to cut wax along the side of the ear-extracting member 30. In addition, shown in FIGS. 18A-18B and 19A-19B, a plurality of holes 188 can be formed along the curved elongated member 180 and into at least one channel 200, 202, 204, 206 to thereby intake wax into the channel. Also, the elongated member 180 can include at least one projecting member 189 capable of guiding earwax into a hole 189 and into a channel 200, 202, 204, 206. In another embodiment shown in FIGS. 19A-C and 20, the shaft 20 can include an aperture 22 therethrough to collect and exhaust wax.

In another embodiment shown in FIGS. 21A-21D, the curved elongated member 180 can be comprised of a first flag member 181 and a second flag member 183. The first and second flag members 181, 183 are attached at one pair of opposing ends of the elongated cross-bar member 190. Each flag member 181, 183 may further comprise an extending wedge portion 185 having a pointed longitudinal edge 187. The longitudinal edge 187 can thereby scrape earwax from inside the ear when the device 10 is rotated. The flag members 181, 183 can also each have at least one aperture 192 therethrough. The apertures 192 in the flag members 181, 183 can further collect wax as the device 10 is rotated during use.

Embodiments of the Present Invention Having a "Shovel" Design

FIGS. 22A-24 illustrate embodiments of the present invention having a shovel-like earwax-extracting member 30. This embodiment of the device 10 can also cut wax at the tip portion 50 while scrape wax along the sides of the earwax-extracting member 30. As shown in FIGS. 22A and 22B, the earwax-extracting member 30 can comprise a body portion 40 having a first 210 and second elongated member 220, each of the elongated members are connected to an end of the shaft 20 of the device 10. To facilitate collection of wax, the elongated members 210, 220 can have a sloped interior surface 230 to cut wax and curved exterior surface 240 to scrape wax along its edges.

Another embodiment of the shovel-like device 10 shown in FIGS. 23A and 23B includes a curved horizontal member 250 connecting the first elongated member 210 and second elongated member 220. The curved horizontal member 250 adds flexibility to the lateral elongated members 210, 220 which can then bend and sweep up wax when the device 10 is rotated in the ear. A third elongated member 260 connected to the curved horizontal member 250 between the first 210 and second 220 elongated members can also further increase dislodging of wax from the ear. All three elongated members 210, 220, 260 can vary in size and shape.

Figure 24:
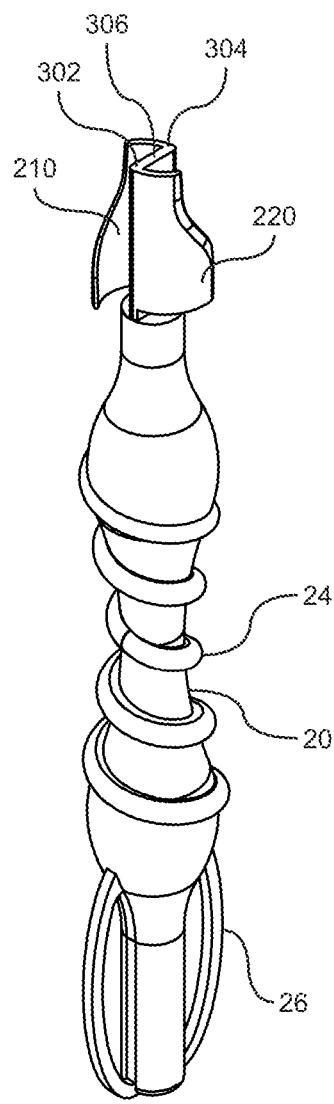
FIG. 24 illustrates a perspective view of an embodiment of a wax removal device having flag members according to the present invention.

In yet another embodiment shown in FIG. 24, the first and second elongated members 210, 220 can be connected to opposing side ends 302, 304 of an elongated vertical bar member 300 that is extending in a direction substantially parallel to the longitudinal axis of the shaft. The elongated vertical bar member 300 can be formed in any shape and is not limited to that shown in FIG. 24.

As will be understood upon using the embodiments of the device 10, one earwax-extracting member 30 can provide multi-functional properties. The tip portion 50 and body portion 40 can provide dual-action structures and mechanisms to remove different forms of wax from the ear at the front end of the device 10 and on the sides of the device 10. In addition, various embodiments utilizing spring structures, ridge structures, openings, tunnels and holes in the device 10 can increase the function of capturing and removing wax in different manners.

A method for removing earwax from an ear canal is also described, the method comprising the steps of providing any of the above embodiments of the earwax removal device 10, inserting the earwax-extracting member 30 of the earwax removal device 10 into the ear canal, rotating the earwax removal device 10 while the earwax-extracting member 30 of the earwax removal device 10 is located in the ear canal, and pulling out the earwax-extracting member 30 of the earwax removal device 10 from the ear canal. Certain embodiments of the device 10, such as those described with a "coil" design above, do not require the rotating step to effectively capture and remove wax from the ear.

While the present invention has been described with regards to particular embodiments, it is recognized that additional variations of the present invention may be devised without departing from the inventive concept. A person skilled in the art would appreciate that exemplary embodiments described hereinabove are merely illustrative of the general principles of the present invention. Other components, configurations, modifications or variations may be employed that are within the scope of the invention. Accordingly, the drawings and description are illustrative and not meant to be a limitation thereof.

All terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Thus, it is intended that the invention cover all embodiments and variations thereof as long as such embodiments and variations come within the scope of the appended claims and their equivalents.

What is claimed is:

1. An earwax removal device comprising:
a shaft having a longitudinal axis;
an earwax-extracting member comprising a central rod having a first end and a second end, the second end connected to an end of the shaft, the central rod extending in a direction substantially parallel to the longitudinal axis of the shaft; and
a helical ridge member characterized as having a spiraling outer edge extending about the central rod, wherein the helical ridge member has a helical spacing coiled along the longitudinal axis of the shaft to direct wax within and along the longitudinal axis of the shaft;
wherein the spiraling outer edge has a notch traversing a surface of the spiraling outer edge and traversing the helical spacing coiled along the longitudinal axis of the shaft, thereby separating the spiraling outer edge of the helical ridge member into a discontinuous upper helical ridge member region and a lower helical ridge member region;
wherein the notch traversing the surface of the spiraling outer edge forms at least one substantially vertical edge within the helical ridge member and is adapted to engage and direct wax toward the second end of the central rod when the earwax removal device is rotated.

2. The earwax removal device of claim 1, the helical ridge member having widths perpendicular to the longitudinal axis of the shaft, wherein widths of the helical ridge member at two different distances from the end of the shaft to which the flexible body is connected are different from each other.

3. The earwax removal device of claim 1, wherein an opening is formed in the first end of the central rod, a hole is formed in the central rod, and a tunnel is formed inside the central rod such that the opening of the central rod and the hole of the central rod are connected to the tunnel.

4. The earwax removal device of claim 1, wherein the notch is a plurality of notches traversing the surface of the spiraling outer edge of the helical ridge member.

5. The earwax removal device of claim 4, wherein the plurality notches are substantially in vertical alignment to each other along the longitudinal axis of the shaft.

6. The earwax removal device of claim 1 wherein the first end of the earwax-extracting member is characterized as having a conical shape, thereby configured to substantially conform to a shape of an eardrum, thereby decreasing a chance of eardrum injury.

7. The earwax removal device of claim 1, wherein the earwax-extracting member is made from a flexible material whereby the earwax-extracting member is capable of compressing and expanding along the longitudinal axis of the shaft to dislodge engaged wax.

8. The earwax removal device of claim 1, wherein the shaft is characterized as having a region of diameter greater than a diameter of the earwax extracting member, thereby configured to limit passage of the earwax extracting member at a narrowing of an ear canal at a bony-cartilaginous junction.

9. The earwax removal device of claim 1, wherein the earwax extraction member is more flexible than the shaft, thereby allowing the earwax extraction member to twist at a different angle than the shaft.

10. The earwax removal device of claim 9, wherein the central rod of the earwax-extracting member is flexible and narrower than the shaft of the earwax removal device, thereby allowing the earwax removal device to bend at a juncture between the earwax-extracting member and the shaft, thereby allowing the earwax removal device to conform to a shape of an ear canal.

11. The earwax removal device of claim 1, wherein the notch is angularly offset from the longitudinal axis of the shaft, thereby forming an angular grinding edge of the spiraling outer edge to engage and scrape wax from an ear canal.

12. An earwax removal device comprising:
a shaft having a longitudinal axis;
an earwax-extracting member comprising a central rod having a first end and a second end, the second end connected to an end of the shaft, the central rod extending in a direction substantially parallel to the longitudinal axis of the shaft; and a helical ridge member characterized as having a spiraling outer edge extending about the central rod, wherein the helical ridge member has a helical spacing coiled along the longitudinal axis of the shaft to direct wax within and along the longitudinal axis of the shaft;

wherein the spiraling outer edge has a notch traversing a surface of the spiraling outer edge and traversing the helical spacing coiled along the longitudinal axis of the shaft, thereby separating the spiraling outer edge of the helical ridge member into a discontinuous upper helical ridge member region and a lower helical ridge member region;

wherein the notch traversing the spiraling outer edge forms at least one substantially vertical edge within the helical ridge member and is adapted to engage and direct wax toward the second end of the central rod when the earwax removal device is rotated;

wherein the earwax-extracting member is made from a flexible material whereby the earwax-extracting member is capable of compressing and expanding along the longitudinal axis of the shaft to dislodge to dislodge engaged wax;

wherein the shaft is characterized as having a region of diameter greater than a diameter of the earwax extracting member, thereby configured to limit passage of the earwax extraction member at a narrowing of an ear canal at a bony-cartilaginous junction;

wherein the earwax extraction member is more flexible than the shaft, thereby allowing the earwax extraction member to twist at a different angle than the shaft;

wherein the central rod of the earwax-extracting member is flexible and narrower than the shaft of the earwax removal device, thereby allowing the earwax removal device to bend at a juncture between the earwax-extracting member and the shaft, thereby allowing the earwax removal device to conform to a shape of an ear canal; and, wherein the notch is angularly offset from the longitudinal axis of the shaft, thereby forming an angular grinding edge of the spiraling outer edge to engage and scrape wax from an ear canal.

\* \* \* \* \*